US008250903B2

(12) United States Patent
McDevitt et al.

(10) Patent No.: US 8,250,903 B2
(45) Date of Patent: Aug. 28, 2012

(54) BIOLOGICAL PARTICLE COLLECTOR AND METHOD FOR COLLECTING BIOLOGICAL PARTICLES

(75) Inventors: James McDevitt, Boston, MA (US); Donald Milton, Lexington, MA (US); Petros Koutrakis, Weston, MA (US); Stephen T. Ferguson, North Billerica, MA (US); Jack M. Wolfson, Jamaica Plain, MA (US)

(73) Assignees: President and Fellows of Harvard College, Cambridge, MA (US); University of Massachusetts, Shrewsbury, MA (US)

( * ) Notice: Subject to any disclaimer, the term of this patent is extended or adjusted under 35 U.S.C. 154(b) by 289 days.

(21) Appl. No.: 12/729,669

(22) Filed: Mar. 23, 2010

(65) Prior Publication Data

US 2010/0242633 A1 Sep. 30, 2010

Related U.S. Application Data

(60) Provisional application No. 61/162,395, filed on Mar. 23, 2009.

(51) Int. Cl.
*G01N 1/22* (2006.01)

(52) U.S. Cl. ..................... 73/23.3; 73/28.01; 73/863.21; 73/863.22; 73/863.41

(58) Field of Classification Search ................... 73/23.2, 73/23.3, 23.31–23.34, 28.01–28.06, 31.01, 73/31.05, 31.07, 863.21, 863.22, 863.44
See application file for complete search history.

(56) References Cited

U.S. PATENT DOCUMENTS

| | | | | |
|---|---|---|---|---|
| 3,665,917 | A * | 5/1972 | Jensen | 600/529 |
| 3,745,991 | A * | 7/1973 | Gauthier et al. | 600/529 |
| 4,133,202 | A | 1/1979 | Marple | |
| 4,321,822 | A | 3/1982 | Marple et al. | |
| 4,796,475 | A | 1/1989 | Marple | |
| 4,926,679 | A | 5/1990 | Dewhurst | |
| 5,233,975 | A * | 8/1993 | Choate | 128/200.14 |
| 5,253,641 | A * | 10/1993 | Choate | 128/200.14 |
| 5,372,126 | A * | 12/1994 | Blau | 128/200.14 |
| 5,437,198 | A | 8/1995 | John | |
| 5,553,795 | A | 9/1996 | Tsai et al. | |
| 5,902,385 | A | 5/1999 | Willeke et al. | |
| 5,904,742 | A | 5/1999 | Teay | |
| 6,176,235 | B1 * | 1/2001 | Benarrouch et al. | 128/200.24 |
| 6,244,096 | B1 * | 6/2001 | Lewis et al. | 73/23.2 |
| 7,013,893 | B2 * | 3/2006 | Wickham et al. | 128/204.23 |
| 7,034,549 | B2 * | 4/2006 | Richardson et al. | 324/636 |
| 7,178,380 | B2 * | 2/2007 | Shekarriz et al. | 73/28.04 |
| 7,416,902 | B2 * | 8/2008 | Pletcher et al. | 436/174 |
| 7,437,908 | B2 * | 10/2008 | Bae et al. | 73/28.02 |
| 7,549,318 | B2 * | 6/2009 | Burtscher et al. | 73/28.02 |
| 2003/0052281 | A1 * | 3/2003 | Rader et al. | 250/461.1 |

(Continued)

OTHER PUBLICATIONS

Demokritou, P., et al.; A high volume apparatus for the condensational growth of ultrafine particles for inhalation toxicological studies, Aerosol Science and Technology 36:1061-1072 (2002).

(Continued)

*Primary Examiner* — David Rogers
(74) *Attorney, Agent, or Firm* — Alan W. Steele; Foley Hoag LLP

(57) ABSTRACT

Provided are devices and methods for the collection of bioaerosols (such as viruses, bacteria, and proteins) from the exhaled breath of humans and/or animals, for the purpose of determining, for example, particle size, generation rate, diseases and interventions for particle release.

27 Claims, 8 Drawing Sheets

[A]

[B]

U.S. PATENT DOCUMENTS

| | | | | |
|---|---|---|---|---|
| 2004/0069047 | A1* | 4/2004 | Coyle et al. | 73/28.04 |
| 2004/0161804 | A1* | 8/2004 | McCash et al. | 435/7.2 |
| 2009/0133513 | A1* | 5/2009 | Davis et al. | 73/864.51 |
| 2009/0137920 | A1* | 5/2009 | Colman et al. | 600/543 |
| 2009/0275015 | A1* | 11/2009 | Bonner | 435/5 |
| 2010/0087749 | A1* | 4/2010 | Tovey | 600/543 |
| 2010/0159575 | A1* | 6/2010 | Chen | 435/287.2 |

OTHER PUBLICATIONS

Fabian, P., et al.; An optimized method to detect influenza virus and human rhinovirus from exhaled breath and the airborne environment, J. Environ. Monit. 11(2): 314-7 (Feb. 2009).

Fabian, M.P., et al.; Influenza virus in human exhaled breath. Abstract. Pan-American Aerobiology Association Annual Symposium, Amherst, MA (Jun. 17, 2008).

Fabian, P., et al.; Influenza virus in human exhaled breath: an observational study, PLoS One, 3(7):e2691 (Jul. 16, 2008).

Gerone, P. J., et al.; Assessment of experimental and natural viral aerosols, Bacteriological Reviews, 30(3): 576-584 (1966).

McDevitt, J., et al.; A new sampler to collect infectious viruses from exhaled breath. American Association of Aerosol Research Annual Conference, Orlando, FL (Oct. 23, 2008).

Orsini, D. A., et al.; Refinements to the particle-into-liquid sampler (PILS) for ground and airborne measurements of water soluble aerosol composition, Atmospheric Environment 37: 1243-1259 (2003).

Orsini, D. A., et al.; a water cyclone to preserve insoluble aerosols in liquid flow—an interface to flow cytometry to detect airborne nucleic acid, Aerosol Science and Technology, 42:343-356 (2008).

* cited by examiner

[A]

[B]

[A]

[B]

BIOLOGICAL PARTICLE COLLECTOR AND METHOD FOR COLLECTING BIOLOGICAL PARTICLES

RELATED APPLICATION

This application claims the benefit of priority to U.S. Provisional Patent Application Ser. No. 61/162,395, filed Mar. 23, 2009; the contents of which are hereby incorporated by reference.

GOVERNMENT SUPPORT

This invention was made with government support under U01 CI000446 awarded by the Centers for Disease Control. The government has certain rights in the invention.

BACKGROUND

Understanding the transmission pathways of influenza and other emerging infectious diseases is essential for assessing risk, providing effective interventions, and minimizing public fear of epidemics and pandemics. Very little information is available on the number and size of particles generated by infected persons, in part due to the limitations of conventional air samplers. For example, conventional air samplers do not efficiently capture fine particles and do not maintain the viability of captured microorganisms. Therefore, a need exists for air samplers that efficiently capture fine particles and maintain the viability of captured microorganisms.

SUMMARY

One aspect of the invention relates to the devices and methods for the collection of bioaerosols (such as viruses, bacteria, and proteins) from the exhaled breath of humans and/or animals, for the purpose of determining, for example, particle size, generation rate, diseases and interventions for particle release. In certain embodiments, the invention relates to samplers which can collect exhaled breath particles and which can be used in viral infectivity analyses. In certain embodiments, the sampler comprises a truncated cone shaped inlet which collects exhaled breath and allows test subjects to comfortably perform various breathing maneuvers (i.e., tidal breathing, coughing, and talking) and also allows subjects to wear a mask or respirator during testing. In certain embodiments, the sampler comprises a 5.0 μm slit inertial impactor that collects particles greater than 5 μm. Subsequently, in certain embodiments, condensation of water vapor is used to grow remaining particles, including fine particles, to a size large enough to be collected efficiently by a 1.0 μm slit inertial impactor and to be deposited into a buffer-containing collector (or other medial particularly suitable for preserving the viability of an airborne biological species).

One embodiment of the invention (referred to herein as "the G-II") was evaluated for efficiency in fine particle (with aerodynamic sizes less than 2.5 micron) collection using nebulized ammonium sulfate aerosols. Comparison of upstream and downstream samples collected on filters and analyzed via ion chromatography showed 96% removal of sulfate aerosols. The results were confirmed using a scanning mobility particle sizer and a condensation particle counter which measured 90-98% fine particle removal efficiencies for sulfate particles from 50-750 μm aerodynamic diameter (AED). The data established that the G-II can efficiently collect submicron-sized viruses from the air stream.

Importantly, in certain embodiments, the samplers disclosed herein enable determination of exhaled breath infectious virus generation rate and allow for the evaluation of simple control strategies, such as wearing a surgical type dust mask to prevent the release of viruses from infected persons.

DETAILED DESCRIPTION

Figure 1A:
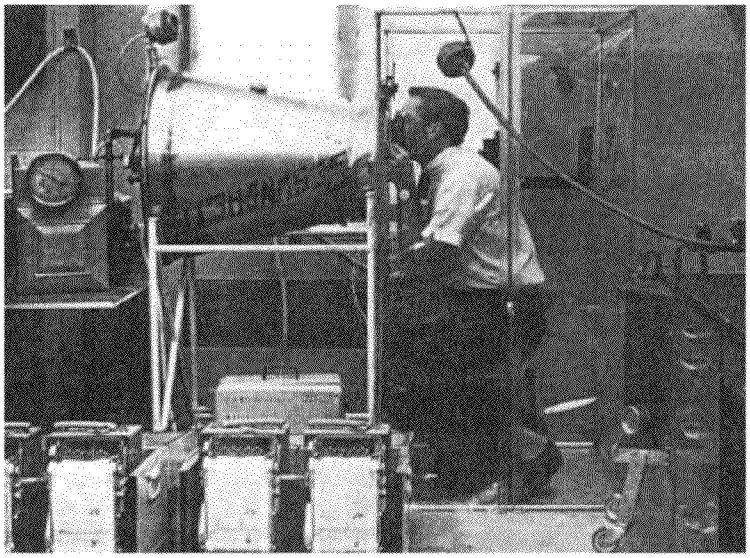
FIG. 1 depicts [A] the original Gesundheit Machine (see FIG. 4 in Gerone et al. *Bact. Rev.* 1966, 30(3), 576-88); and [B] the Gesundheit Machine II ("the G-II").
Figure 1B:
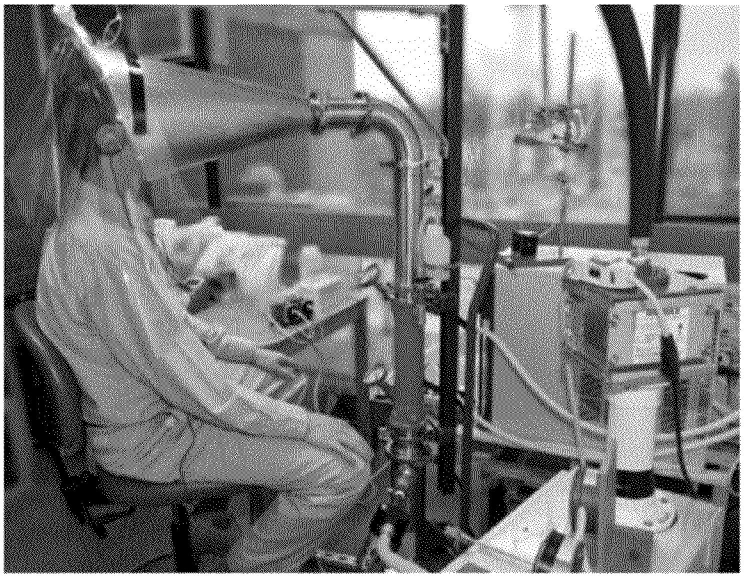
Figure 2:
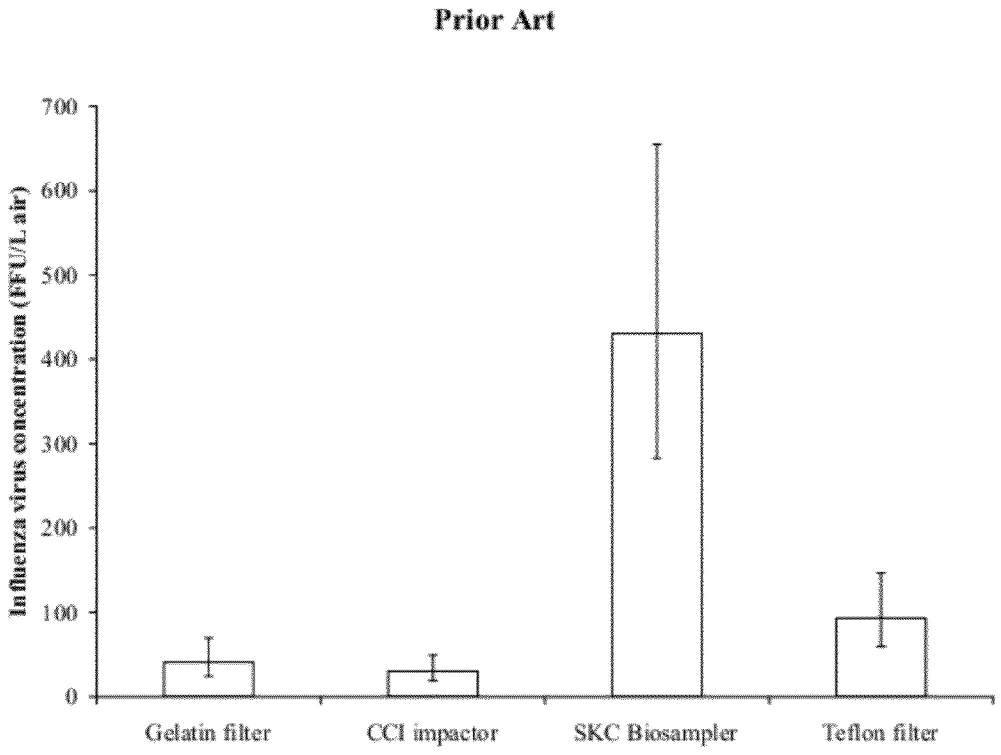
FIG. 2 depicts a graph showing infectious virus recovery for virus collected with a gelatin filter, a Controlled Cortical Impact (CCI) impactor, a SKC biosampler (see U.S. Pat. Nos. 5,902,385 and 5,904,752; hereby incorporated by reference), and a polytetrafluoroethylene (PTFE)® filter.
Figure 3:
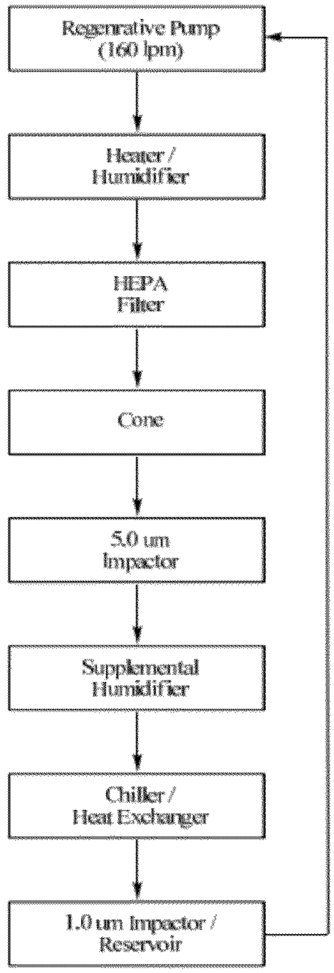
FIG. 3 depicts an embodiment of the invention and a flow chart depicting the same.
Figure 3:
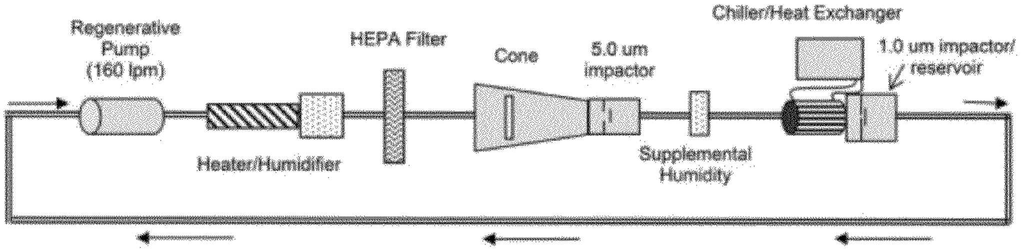
Figure 4:
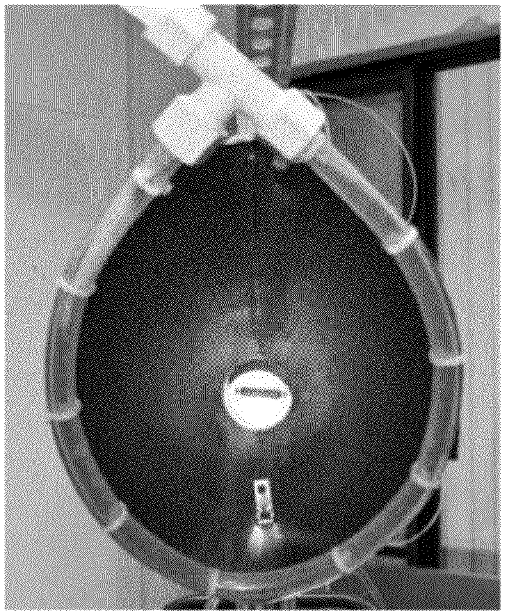
FIG. 4 depicts [A] one embodiment of a slit inertial impactor for greater than 5 μm particles (as viewed from outside the cone); and [B] one embodiment of a fine and ultrafine particle collector containing a supplemental humidifier, a chiller/heat exchanger, and an inertial impactor-collection reservoir.
Figure 4:
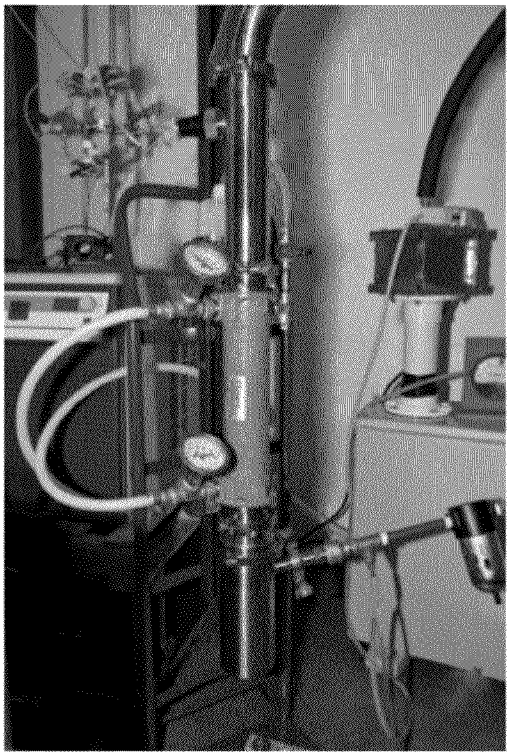
Figure 5:
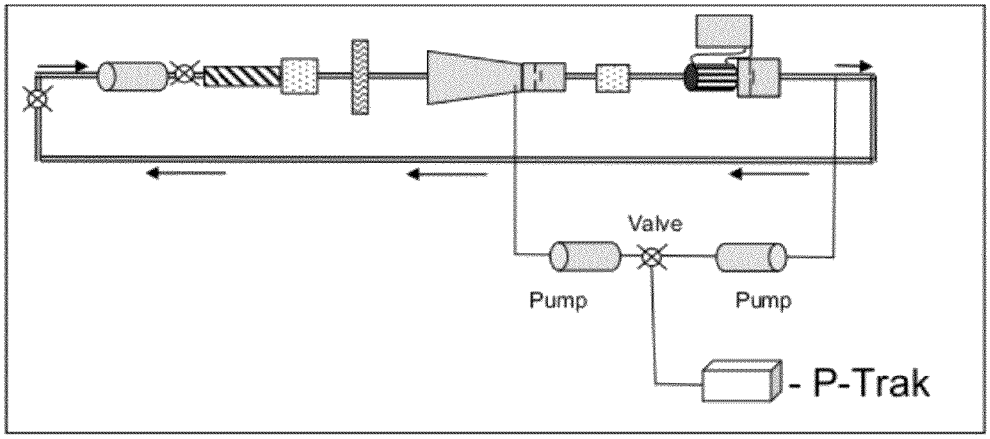
FIG. 5 depicts [A] one embodiment of the invention which includes a P-Trak ultrafine particle counter which is able to count all particles less than 1.0 μm; and [B] another embodiment of the invention which includes a SMPS/CPC (scanning mobility particle sizer in conjunction with a condensation particle counter. These embodiments can be used for determining collection efficiency.
Figure 5:
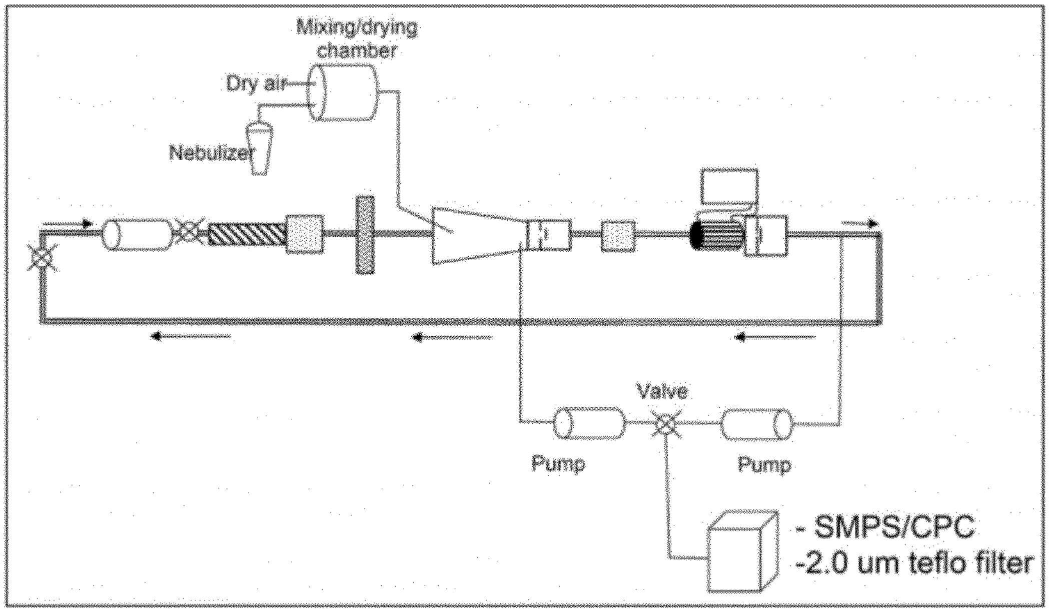
Figure 6:
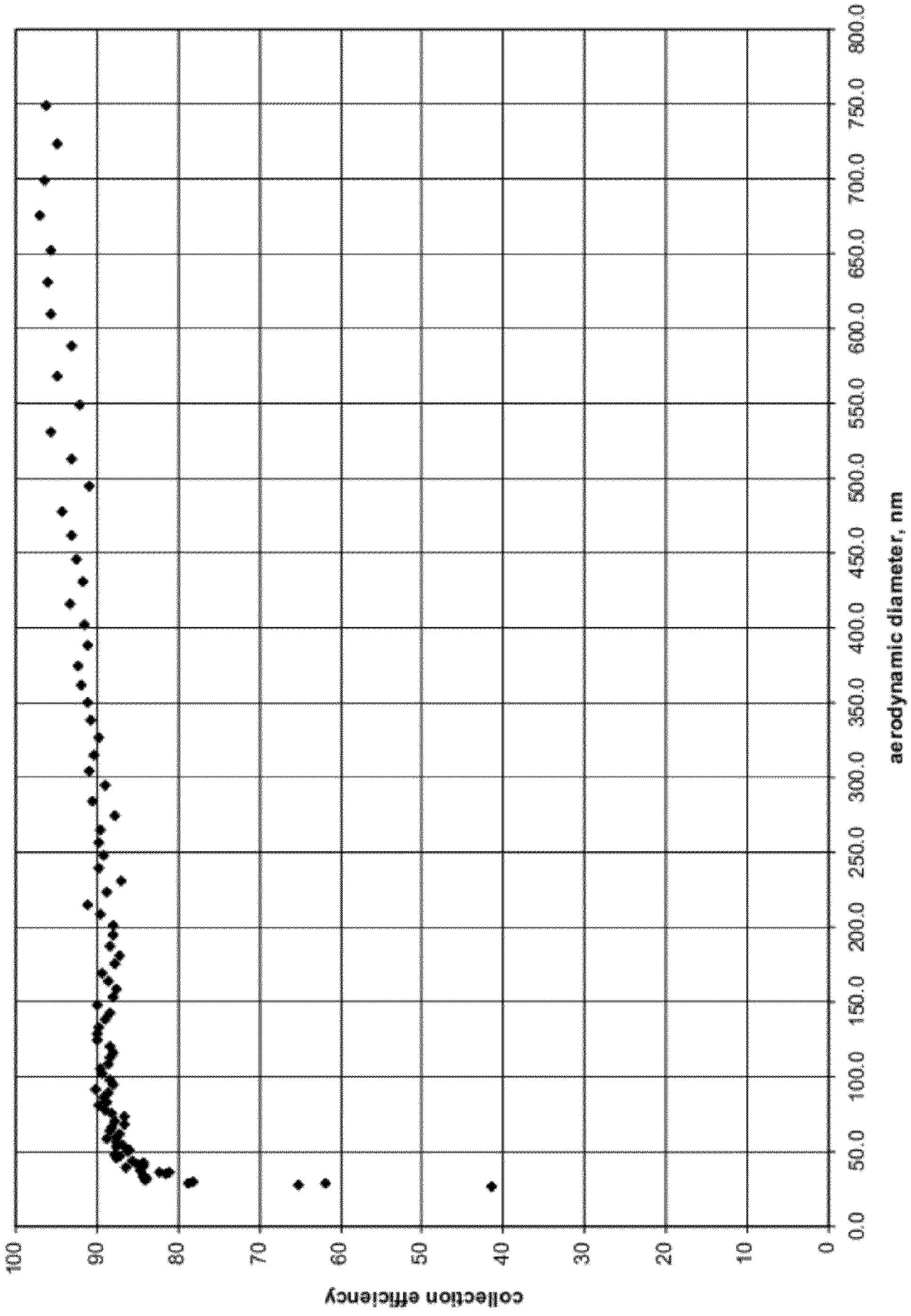
FIG. 6 depicts a graph showing collection efficiency as measured by SMPS.
Figure 7:
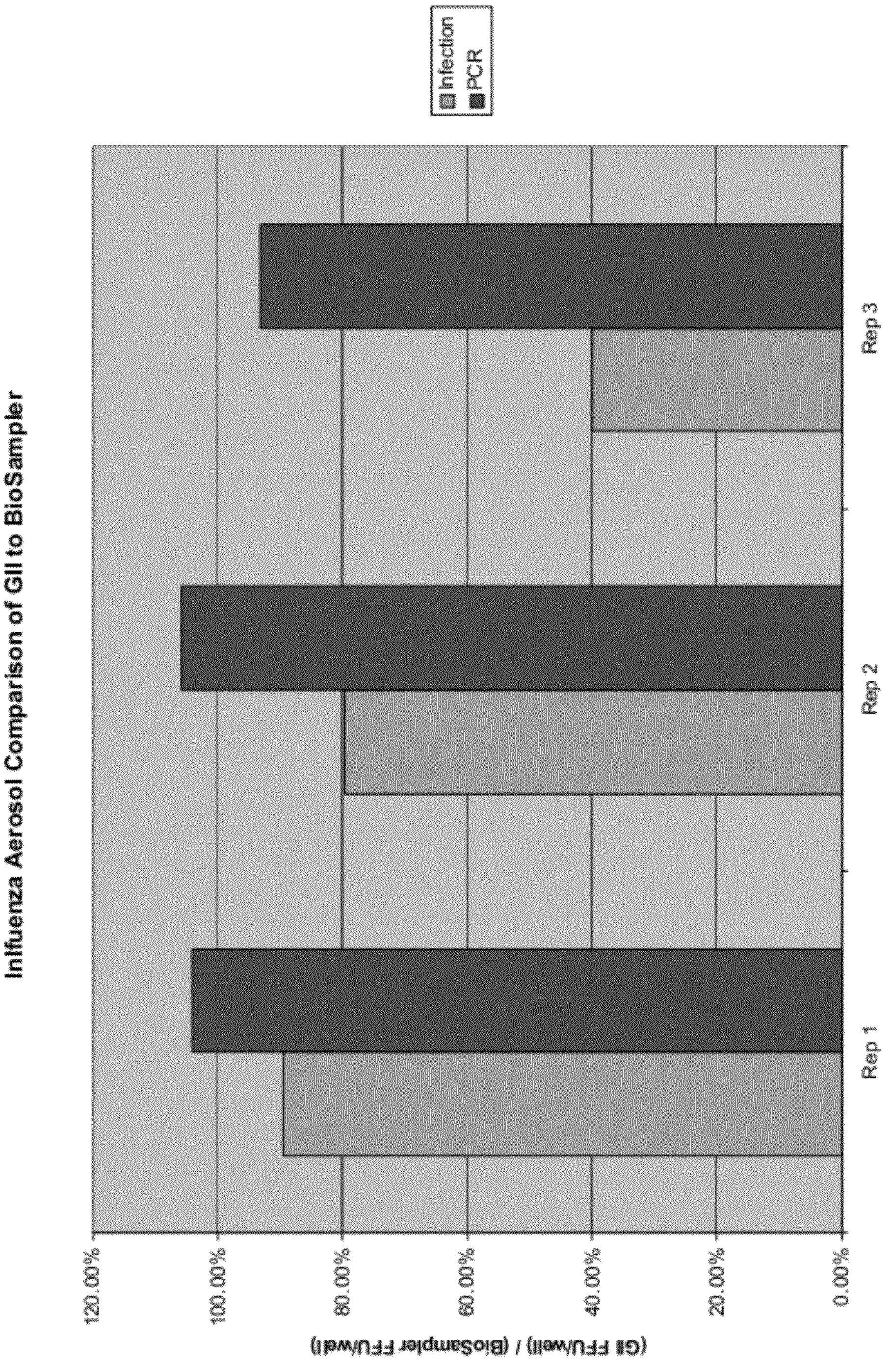
FIG. 7 depicts a graph showing influenza aerosol (H1N1 PR8) in comparison with the G-II to a SKC Biosampler. qPCR was used to determine "total virus" recovery. A cell culture assay was used to determine infectivity.
Figure 8:
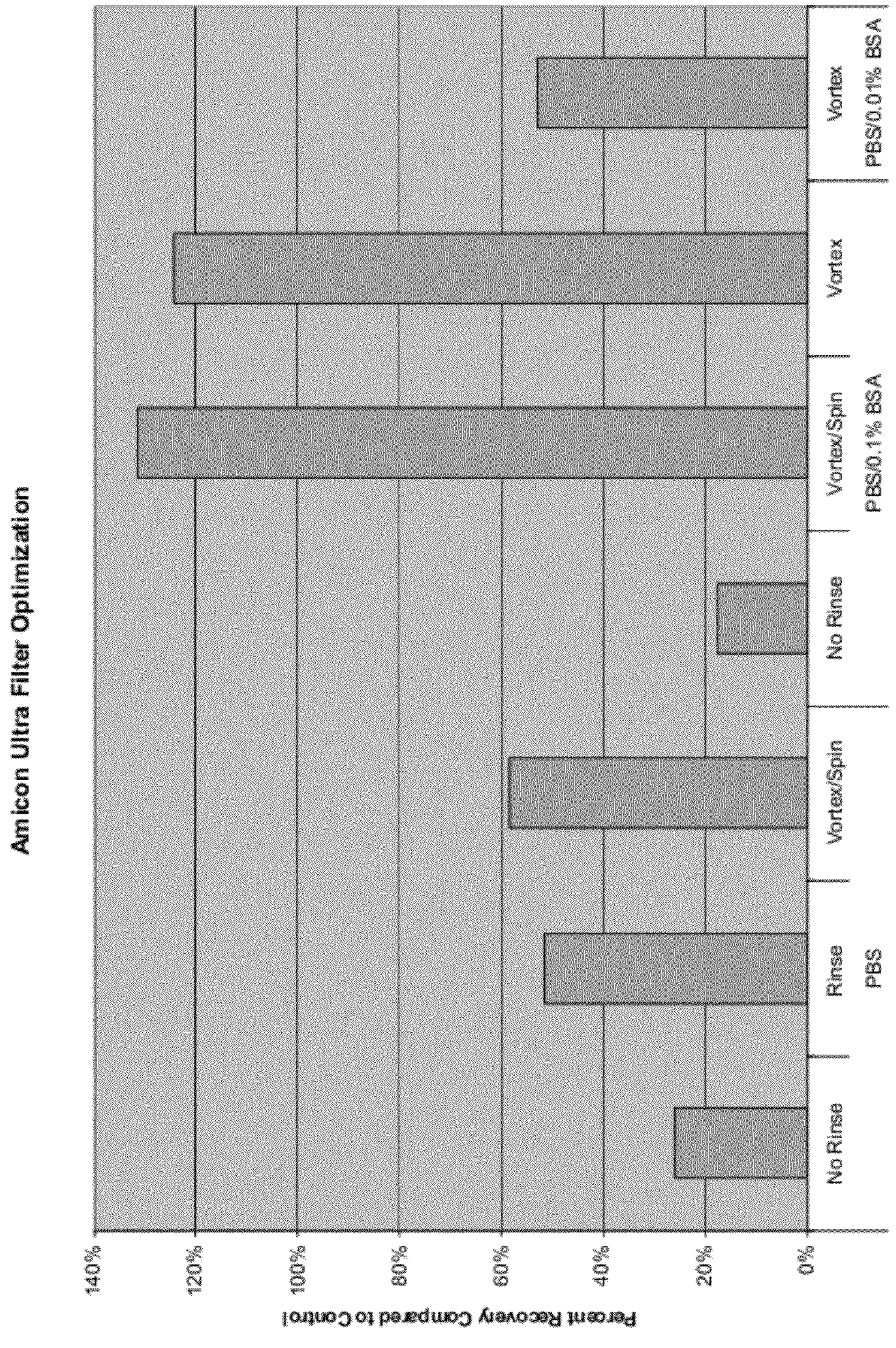
FIG. 8 depicts a graph showing Amicon ultra filter optimization with PBS, PBS with 0.1% BSA and PBS with 0.01% BSA.

Certain aspects of the invention relate to the detection and quantification of viable viruses in exhaled breath, including their presence, number and general size. While aspects of the invention will be described below in relation to measuring viruses in exhaled breath, the invention is not limited to the particular embodiments described.

One aspect of the invention relates to collecting exhaled breath particles, such as viruses and proteins, while maintaining the structure and integrity of the particles for later analysis. For example, in certain embodiments, an obliquely truncated cone shaped inlet, supplied with humidified make up air, collects exhaled breath and allows test subjects to comfortably perform various breathing maneuvers (i.e., tidal breathing, coughing, and talking) The cone design also allows individuals to wear a mask or respirator during collection for the purpose to testing mask particle removal efficiencies. In certain embodiments, a disk in the cone can be used to collect large ballistic droplets. In certain embodiments, a slit inertial impactor down stream of the cone collects particles with sizes greater than or equal to 5.0 μm. Subsequently, in certain embodiments, condensation of water vapor is used to grow remaining particles, including fine and ultrafine particles, to a size large enough to be efficiently collected by a 1.0 μm slit inertial impactor and be deposited into a buffer-containing collector.

Another aspect of the invention relates to the determination of exhaled infectious particle generation rate and the evaluation of simple control strategies, such as wearing a surgical type dust mask, to minimize the release of infectious particles from infected persons.

Another aspect of the invention relates to a device that is capable of collecting fine biological particles, from high volumes of air, with high efficiency, while maintaining biological integrity of the aerosol. In addition, in certain embodiments the collectors are designed to allow comfortable and efficient collection of exhaled breath, even when a person is wearing a mask. For example, in certain embodiments the invention relates to the collection of non-infectious particles, such as proteins, from exhaled breath. Remarkably, the design of certain collectors described herein minimize the denaturing of proteins and allows for the collection of fine particles containing proteins that are biomarkers for pulmonary inflammation and other pathology.

DEFINITIONS

By "humidifier" is meant a device which increases the moisture content of a gas, such as air, and a pump, or similar device, to move said gas.

By "aerosol" is meant a mixture that includes particles suspended in a gas, such as air.

By "steam generator" is meant a device to inject a small turbulent flow of steam into the aerosol to increase the relative humidity to near saturation at a relatively warm temperature. This increase in relative humidity makes it possible to subsequently create supersaturation of water vapor by rapidly cooling the high humidity aerosol using a chiller/heat exchanger (as defined below). In the chiller, water vapor condenses on the small particles in the aerosol, causing them to grow into larger water droplets which can then be collected downstream by inertial methods, for example, with an inertial impactor.

By "chiller/heat exchanger" is meant a device through which the aerosol is allowed to pass, which typically consists of a series of cylindrical tubes surrounded by a hollow jacket through which a cold liquid is passed. The passage of the aerosol through this device causes a reduction in the temperature of the aerosol to just above the freezing point of water. Because the absolute equilibrium vapor pressure of water at this low temperature is several times lower than that of the humidified aerosol that enters the device, so-called "supersaturation" occurs within the device, with the result that excess water vapor condenses on the fine particles in the aerosol, causing them to grow to much larger sizes.

By "series" is meant that multiple stages of a system are arranged so that an aerosol can sequentially pass through each stage of the system.

By "acceleration nozzle" is meant a jet through which a gas sample is passed and which increases the mean velocity of the gas sample to a value sufficient to impart enough momentum to particles above a specific size that the particles are able to impact on an impaction substrate as described herein. For example, a gas sample may be sucked through a nozzle having a reduced cross-sectional area relative to a source of gas using a downstream vacuum pump. An acceleration nozzle may be of any shape, such as round or slit shaped. A round acceleration nozzle or jet has a round opening through which gas exits. The nozzle body may be cylindrical. A slit shaped acceleration nozzle or jet has a rectangular opening, including narrow and nearly square-shaped openings, through which gas exits.

By "impacting particles" is meant particles in the gas sample that have acquired sufficient momentum after passage through an acceleration jet to pass through the air streamlines downstream of the jet and strike an impaction substrate. Particles in the gas sample that do not acquire enough momentum do not cross the streamlines and do not reach the substrate and are not collected. Impacting is distinct from the process of filtering, where the entire gas sample passes through a filter and particles are retained on the filter. In the process of impacting, all or almost all of the gas sample does not pass through the substrate.

By "impaction substrate" is meant a component having a surface onto which particles can be impacted and collected. The surface does not function as a filter, as all or almost all of the gas sample does not pass through the impaction substrate, but rather passes, for example, over, along, or around the impaction substrate. Only particles in the gas sample that acquire sufficient momentum from the acceleration jet strike the impaction substrate. The remaining gas sample, together with particles that do not have enough momentum to impact the substrate surface, passes to the side and/or around the substrate. The impaction substrate absorbs energy from the accelerated particles and particles larger than a particular size (aerodynamic diameter) are collected. The greater the velocity of the gas sample through the acceleration jet, the smaller the aerodynamic diameter of the particles that impact on the substrate. Thus, by adjusting the velocity of the gas sample through the acceleration jet, particles larger than a desired size range can be collected. Examples of materials for use as impaction substrates are flat plates made of inert materials, such as polytetrafluoroethylene (PTFE).

An "inertial impactor" typically refers to a single unit comprising of an air inlet, an acceleration nozzle, and an impaction plate. At the acceleration nozzle exit, the airstreams turns sharply and particles larger than a certain diameter (referred to as the impactor's cut off size) impinge on the collection surface due to inertial forces. Exemplary inertial impactors are discussed in U.S. Pat. Nos. 5,553,795, 5,437,198, 4,926,679, 4,796,475, 4,321,822, and 4,133,202; all of which are hereby incorporated by reference.

By "buffer solution" is meant an aqueous solution consisting of a mixture of a weak acid and its conjugate base or a weak base and its conjugate acid. It has the property that the pH of the solution changes very little when a small amount of acid or base is added to it.

Aerosol Particle Collection Devices

One aspect of the invention relates to an aerosol particle collection device comprising:

a pump;

a humidifier;

a filter;

an inlet for a gas sample;

a first inertial impactor;

a steam generator;

a chiller/heat exchanger;

a second inertial impactor; and a collection reservoir;

wherein the pump, humidifier, filter, inlet, first inertial impactor, steam generator, chiller/hear exchanger, second inertial impactor and collection reservoir are in series;

the gas sample comprises an aerosol;

the collection reservoir collects particles trapped by the second inertial impactor;

the inlet is downstream from the humidifier;

the first inertial impactor is downstream from the inlet;

the steam generator is downstream from the first inertial impactor;

the chiller/heat exchanger is downstream from the steam generator;

the second inertial impactor is downstream from the chiller/heat exchanger; and the collection reservoir contains a liquid and is downstream from the second inertial impactor.

In certain embodiments, the present invention relates to any of the aforementioned devices, further comprising a disk inside the inlet which can be used to collect large ballistic droplets.

In certain embodiments, the present invention relates to any of the aforementioned devices, wherein the pump creates a flow of between about 150 L/min and about 200 L/min.

In certain embodiments, the present invention relates to any of the aforementioned devices, wherein the pump creates a flow of about 160 L/min.

In certain embodiments, the present invention relates to any of the aforementioned devices, wherein the filter is a HEPA filter.

In certain embodiments, the present invention relates to any of the aforementioned devices, wherein the inlet is an obliquely truncated cone shaped inlet.

In certain embodiments, the present invention relates to any of the aforementioned devices, wherein the first inertial impactor is a first slit inertial impactor.

In certain embodiments, the present invention relates to any of the aforementioned devices, wherein the first inertial impactor is a first slit inertial impactor; and the first slit inertial impactor has a slit with a cut point of about 5.0 μm.

In certain embodiments, the present invention relates to any of the aforementioned devices, wherein the first inertial impactor comprises an impaction substrate which is a flat impaction plate.

In certain embodiments, the present invention relates to any of the aforementioned devices, wherein the flat impaction plate comprises poly(tetrafluoroethylene).

In certain embodiments, the present invention relates to any of the aforementioned devices, wherein the chiller/heat exchanger increases the diameter of at least some of the aerosol particles in the gas sample which were not removed by the first inertial impactor.

In certain embodiments, the present invention relates to any of the aforementioned devices, wherein the second inertial impactor is a second slit inertial impactor.

In certain embodiments, the present invention relates to any of the aforementioned devices, wherein the second inertial impactor is a second slit inertial impactor; and the second slit inertial impactor has a slit with a cut point of about 1.0 μm.

In certain embodiments, the present invention relates to any of the aforementioned devices, wherein the gas sample comprises one or more viruses, bacteria, fungi, cells, nucleic acids or proteins.

In certain embodiments, the present invention relates to any of the aforementioned devices, wherein the gas sample comprises a protein.

In certain embodiments, the present invention relates to any of the aforementioned devices, wherein the gas sample comprises a virion.

In certain embodiments, the present invention relates to any of the aforementioned devices, wherein the liquid in the collection reservoir comprises a buffer solution.

In certain embodiments, the present invention relates to any of the aforementioned devices, wherein the liquid in the collection reservoir comprises phosphate buffered saline (PBS), 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 4-2-hydroxyethyl-1-piperazine-ethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate) or 2-(N-morpholino)ethanesulfonic acid (MES).

In certain embodiments, the present invention relates to any of the aforementioned devices, wherein the liquid in the collection reservoir is phosphate buffered saline (PBS).

In certain embodiments, the present invention relates to any of the aforementioned devices, wherein the liquid-containing reservoir further comprises bovine serum albumin (BSA).

In certain embodiments, the present invention relates to any of the aforementioned devices, further comprising a syringe pump in fluid communication with the collection reservoir. In certain embodiments, the syringe pump can be used to add concentrated buffer to the collection reservoir. In certain embodiments, the rate of addition of buffer/BSA solution to the collection reservoir is equal to the rate of production of condensed water vapor that occurs in the chiller/heat exchanger, allowing the buffer/BSA solution to be diluted to optimum concentration by the distilled water in real time.

In certain embodiments, the present invention relates to any of the aforementioned devices, wherein the gas sample is exhaled breath.

Methods

One aspect of the invention relates to a method of separating and collecting aerosol particles present in a gas sample, the method comprising introducing an aerosol into an aerosol particle collection device; and collecting the aerosol particles from the aerosol in a collection reservoir; wherein said aerosol particle collection device comprises:

a pump;

a humidifier;

a filter;

an inlet for a gas sample;

a first inertial impactor;

a steam generator;

a chiller/heat exchanger;

a second inertial impactor; and a collection reservoir;

wherein the pump, humidifier, filter, inlet, first inertial impactor, steam generator, chiller/hear exchanger, second inertial impactor and collection reservoir are in series;

the gas sample comprises an aerosol;

the collection reservoir collects particles trapped by the second inertial impactor;

the inlet is downstream from the humidifier;

the first inertial impactor is downstream from the inlet;

the steam generator is downstream from the first inertial impactor;

the chiller/heat exchanger is downstream from the steam generator;

the second inertial impactor is downstream from the chiller/heat exchanger; and the collection reservoir contains a liquid and is downstream from the second inertial impactor.

In certain embodiments, the present invention relates to any of the aforementioned methods, further comprising the step of centrifugation to concentration the aerosol particles collected in the collection reservoir, thereby forming a condensate.

In certain embodiments, the present invention relates to any of the aforementioned methods, further comprising the step of centrifugation to concentration the aerosol particles collected in the collection reservoir, thereby forming a condensate; adding serum albumin to the resulting condensate; and vortexing the condensate/serum albumin mixture.

In certain embodiments, the present invention relates to any of the aforementioned methods, wherein the gas sample is provided by a subject.

In certain embodiments, the present invention relates to any of the aforementioned methods, wherein the subject is wearing a mask.

In certain embodiments, the present invention relates to any of the aforementioned methods, wherein at least 50% of the aerosol particles present in the gas sample are collected. In certain embodiments, the present invention relates to any of the aforementioned methods, wherein at least 60% of the aerosol particles present in the gas sample are collected. In certain embodiments, the present invention relates to any of the aforementioned methods, wherein at least 70% of the aerosol particles present in the gas sample are collected. In certain embodiments, the present invention relates to any of the aforementioned methods, wherein at least 80% of the aerosol particles present in the gas sample are collected. In certain embodiments, the present invention relates to any of the aforementioned methods, wherein at least 90% of the aerosol particles present in the gas sample are collected.

In certain embodiments, the present invention relates to any of the aforementioned devices, further comprising a disk inside the inlet which can be used to collect large ballistic droplets.

In certain embodiments, the present invention relates to any of the aforementioned methods, wherein the pump creates a flow of between about 150 L/min and about 200 L/min.

In certain embodiments, the present invention relates to any of the aforementioned methods, wherein the pump creates a flow of about 160 L/min.

In certain embodiments, the present invention relates to any of the aforementioned methods, wherein the filter is a HEPA filter.

In certain embodiments, the present invention relates to any of the aforementioned methods, wherein the inlet is an obliquely truncated cone shaped inlet.

In certain embodiments, the present invention relates to any of the aforementioned methods, wherein the first inertial impactor is a first slit inertial impactor.

In certain embodiments, the present invention relates to any of the aforementioned methods, wherein the first inertial impactor is a first slit inertial impactor; and the first slit inertial impactor has a slit with a cut point of about 5.0 μm.

In certain embodiments, the present invention relates to any of the aforementioned methods, wherein the first inertial impactor comprises an impaction substrate which is a flat impaction plate.

In certain embodiments, the present invention relates to any of the aforementioned methods, wherein the flat impaction plate comprises PTFE.

In certain embodiments, the present invention relates to any of the aforementioned methods, wherein the chiller/heat exchanger increases the diameter of at least some of the aerosol particles in the gas sample which were not removed by the first inertial impactor.

In certain embodiments, the present invention relates to any of the aforementioned methods, wherein the second inertial impactor is a second slit inertial impactor.

In certain embodiments, the present invention relates to any of the aforementioned methods, wherein the second inertial impactor is a second slit inertial impactor; and the second slit inertial impactor has a slit with a cut point of about 1.0 μm.

In certain embodiments, the present invention relates to any of the aforementioned methods, wherein the gas sample comprises one or more viruses, bacteria, fungi, cells, nucleic acids or proteins.

In certain embodiments, the present invention relates to any of the aforementioned methods, wherein the gas sample comprises a protein.

In certain embodiments, the present invention relates to any of the aforementioned methods, wherein the gas sample comprises a virion.

In certain embodiments, the present invention relates to any of the aforementioned methods, wherein the collected aerosol particles comprises one or more viruses, bacteria, fungi, cells, nucleic acids or proteins.

In certain embodiments, the present invention relates to any of the aforementioned methods, wherein the collected aerosol particles comprise a protein.

In certain embodiments, the present invention relates to any of the aforementioned methods, wherein the collected aerosol particles comprise a virion.

In certain embodiments, the present invention relates to any of the aforementioned methods, wherein the collected aerosol particles are not degraded upon collection.

In certain embodiments, the present invention relates to any of the aforementioned methods, wherein the collected aerosol particles are still viable (e.g., able to be cultured) after collection.

In certain embodiments, the present invention relates to any of the aforementioned methods, wherein the liquid in the collection reservoir comprises a buffer.

In certain embodiments, the present invention relates to any of the aforementioned methods, wherein the liquid in the collection reservoir comprises phosphate buffered saline (PBS), 3-{[tris(hydroxymethyl)methyl]amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 4-2-hydroxyethyl-1-piperazine-ethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate) or 2-(N-morpholino)ethanesulfonic acid (MES).

In certain embodiments, the present invention relates to any of the aforementioned methods, wherein the liquid in the collection reservoir is phosphate buffered saline (PBS).

In certain embodiments, the present invention relates to any of the aforementioned methods, wherein the liquid-containing reservoir further comprises bovine serum albumin (BSA).

In certain embodiments, the present invention relates to any of the aforementioned methods, further comprising a syringe pump in fluid communication with the collection reservoir. In certain embodiments, the syringe pump can be used to add concentrated buffer/BSA solution to the collection reservoir. In certain embodiments, the rate of addition of buffer/BSA solution to the collection reservoir is equal to the rate of production of condensed water vapor that occurs in the chiller/heat exchanger, allowing the buffer/BSA solution to be diluted to optimum concentration by the distilled water in real time.

In certain embodiments, the present invention relates to any of the aforementioned methods, wherein the gas sample is exhaled breath.

EXEMPLIFICATION

The invention now being generally described, it will be more readily understood by reference to the following exemplification, which is included merely for purposes of illustration of certain aspects and embodiments of the present invention, and is not intended to limit the invention.

An exhaled breath collection device, called the G-II, was designed to collect exhaled breath particles for use in viral infectivity analyses. The G-II was evaluated for fine particle collection efficiency with nebulized ammonium sulfate aerosols. Comparison of up and downstream samples collected on filters and analyzed via ion chromatography showed 96% removal of sulfate aerosols. These results were confirmed using a scanning mobility particle sizer and a condensation particle counter which measured 90-98% fine particle removal efficiencies for sulfate particles from 50-750 μm AED.

The collection efficiency of the G-II for collection of artificially generated influenza aerosols was compared with a reference collection method (BioSampler, SKC, Inc). Fluorescent focus reduction cell culture assay and qPCR was used. The qPCR results showed a 100% collection efficiency when compared with the reference method, while cell culture results varied from less than 10% to 86% efficiency. These results suggested that the G-II is efficiently collecting virus particles, but some of the viruses were being inactivated during the collection process.

Virus survival in the condensate can be increased to nearly 100% by adding concentrated buffer and bovine serum albumin (BSA) to the G-II collector reservoir during sample collection via syringe pump. In addition, losses during concentration with the spin filters can be decreased to nearly 0% through the addition of BSA to the condensate and adding a novel vortex step after centrifugation.

INCORPORATION BY REFERENCE

All of the U.S. patents and U.S. published patent applications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An aerosol particle collection device comprising:

a pump;

a humidifier;

a filter;

an inlet for a gas sample;

a first inertial impactor;

a steam generator;

a chiller/heat exchanger;

a second inertial impactor; and a collection reservoir;

wherein the pump, humidifier, filter, inlet, first inertial impactor, steam generator, chiller/heat exchanger, second inertial impactor and collection reservoir are in series;

the gas sample comprises an aerosol;

the collection reservoir collects particles trapped by the second inertial impactor;

the inlet is downstream from the humidifier;

the first inertial impactor is downstream from the inlet;

the steam generator is downstream from the first inertial impactor;

the chiller/heat exchanger is downstream from the steam generator;

the second inertial impactor is downstream from the chiller/heat exchanger; and the collection reservoir contains a liquid and is downstream from the second inertial impactor.

2. The device of claim 1, further comprising a disk inside the inlet.

3. The device of claim 1 or 2, wherein the pump creates a flow of between about 150 L/min and about 200 L/min.

4. The device of claim 1 or 2, wherein the pump creates a flow of about 160 L/min.

5. The device of claim 1, wherein the filter is a HEPA filter.

6. The device of claim 1, wherein the inlet is an obliquely truncated cone shaped inlet.

7. The device of claim 1, wherein the first inertial impactor is a first slit inertial impactor.

8. The device of claim 1, wherein the first inertial impactor is a first slit inertial impactor; and the first slit inertial impactor has a slit with a cut point of about 5.0 μm.

9. The device of claim 1, wherein the first inertial impactor comprises an impaction substrate which is a flat impaction plate.

10. The device of claim 9, wherein the flat impaction plate comprises poly(tetrafluoroethylene).

11. The device of claim 1, wherein the chiller/heat exchanger increases the diameter of at least some of the aerosol particles in the gas sample which were not removed by the first inertial impactor.

12. The device of claim 1, wherein the second inertial impactor is a second slit inertial impactor.

13. The device of claim 1, wherein the second inertial impactor is a second slit inertial impactor; and the second slit inertial impactor has a slit with a cut point of about 1.0 μm.

14. The device of claim 1, wherein the gas sample comprises one or more viruses, bacteria, fungi, cells, nucleic acids or proteins.

15. The device of claim 1, wherein the gas sample comprises a protein.

16. The device of claim 1, wherein the gas sample comprises a virion.

17. The device of claim 1, wherein the liquid in the collection reservoir comprises a buffer solution.

18. The device of claim 1, wherein the liquid in the collection reservoir comprises phosphate buffered saline (PBS), 3-{[tris(hydroxymethyl)methyl]-amino}propanesulfonic acid (TAPS), N,N-bis(2-hydroxyethyl)glycine (Bicine), tris(hydroxymethyl)methylamine (Tris), N-tris(hydroxymethyl)methylglycine (Tricine), 4-2-hydroxyethyl-1-piperazine-ethanesulfonic acid (HEPES), 2-{[tris(hydroxymethyl)methyl]amino}ethanesulfonic acid (TES), 3-(N-morpholino)propanesulfonic acid (MOPS), piperazine-N,N'-bis(2-ethanesulfonic acid) (PIPES), dimethylarsinic acid (Cacodylate) or 2-(N-morpholino)ethanesulfonic acid (MES).

19. The device of claim 1, wherein the liquid in the collection reservoir is phosphate buffered saline (PBS).

20. The device of claim 1, wherein the liquid-containing reservoir further comprises bovine serum albumin (BSA).

21. The device of claim 1, further comprising a syringe pump in fluid communication with the collection reservoir.

22. The device of claim 1, wherein the gas sample is exhaled breath.

23. A method of separating and collecting aerosol particles present in a gas sample, the method comprising introducing an aerosol into an aerosol particle collection device; and collecting the aerosol particles from the aerosol in a collection reservoir; wherein said aerosol particle collection device is an aerosol protection device of claim 1.

24. The method of claim 23, further comprising the step of centrifugation to concentrate the aerosol particles collected in the collection reservoir, thereby forming a condensate.

25. The method of claim 24, further comprising adding serum albumin to the resulting condensate; and vortexing the condensate/serum albumin mixture.

26. The method of one of claims 23-25, wherein the gas sample is provided by a subject.

27. The method of claim 26, wherein the subject is wearing a mask.

* * * * *